US009604015B2

(12) United States Patent
Gramage Pina

(10) Patent No.: US 9,604,015 B2
(45) Date of Patent: Mar. 28, 2017

(54) SINGLE-USE SYRINGE

(75) Inventor: Ma. Lourdes Gramage Pina, Valencia (ES)

(73) Assignee: Ma. Lourdes Gramage Piña, Valencia (ES)

( * ) Notice: Subject to any disclaimer, the term of this patent is extended or adjusted under 35 U.S.C. 154(b) by 920 days.

(21) Appl. No.: 13/988,189

(22) PCT Filed: Nov. 18, 2010

(86) PCT No.: PCT/ES2010/000469
§ 371 (c)(1),
(2), (4) Date: Aug. 1, 2013

(87) PCT Pub. No.: WO2012/066151
PCT Pub. Date: May 24, 2012

(65) Prior Publication Data
US 2013/0310741 A1  Nov. 21, 2013

(51) Int. Cl.
*A61M 5/50* (2006.01)
*A61M 5/31* (2006.01)
*A61M 5/315* (2006.01)

(52) U.S. Cl.
CPC ........ *A61M 5/5066* (2013.01); *A61M 5/3129* (2013.01); *A61M 5/31511* (2013.01); *A61M 5/502* (2013.01); *A61M 2005/5073* (2013.01)

(58) Field of Classification Search
CPC .............. A61M 5/5006; A61M 5/3129; A61M 5/31511; A61M 2005/5073; A61M 2005/5033
See application file for complete search history.

(56) References Cited

U.S. PATENT DOCUMENTS 2,720,880 A * 10/1955 Whitaker ................ A61M 5/24
604/232
4,233,975 A * 11/1980 Yerman ................ A61M 5/286
604/110
(Continued)

FOREIGN PATENT DOCUMENTS

CN         200966820 Y      10/2007
EP         0 409 134 A1      1/1991
(Continued)

OTHER PUBLICATIONS

International Search Report for International Application No. PCT/ES2010/000469, Mailed Jul. 21, 2011.

*Primary Examiner* — Andrew Gilbert
(74) *Attorney, Agent, or Firm* — Pearl Cohen Zedek Latzer Baratz LLP

(57) ABSTRACT

The present invention relates to a single-use syringe comprising a barrel (10) having an internal surface defining a chamber for retaining a fluid, a plunger (1) formed by an elongated body including a plurality of longitudinal fins (2) and optionally a piston (3) connected to the end of the plunger close to the needle, the external surface of the piston or of the end of the plunger in the case of not including a piston being in leak-tight connection with the internal surface of the barrel, where the barrel has a general external shape of a cylinder of revolution with a constant radius circular base and a variable internal shape, forming the wall of the barrel with variable thickness, generating a chamber inside which a plunger incorporating a plurality of fins (2) slides; each of the longitudinal fins (2) of the plunger has a constant height along its entire length but different from that of at least one of the other fins, which height is suitable in each fin so that the plunger (1) can be inserted tightly without the capability of rotating about itself through the space defined by the variable internal radius of the barrel; the (Continued)

length of at least one of the fins is also different from the length of at least one of the other fins so that the plunger includes a weakened area in the form of a hole at the end of the plunger close to the needle; the barrel further comprises at least two grooves in the internal face of the barrel, at least one being located in the distal part (8) and at least one in the proximal part (9) of the barrel with respect to the needle.

15 Claims, 9 Drawing Sheets

(56) References Cited

U.S. PATENT DOCUMENTS

| | | | | |
|---|---|---|---|---|
| 4,391,272 | A * | 7/1983 | Staempfli | A61M 5/5013 |
| | | | | 604/110 |
| 4,781,684 | A * | 11/1988 | Trenner | A61M 5/5013 |
| | | | | 604/110 |
| 4,826,483 | A * | 5/1989 | Molnar, IV | A61M 5/5013 |
| | | | | 604/110 |
| 4,915,692 | A * | 4/1990 | Verlier | A61M 5/5013 |
| | | | | 604/110 |
| 5,019,045 | A * | 5/1991 | Lee | A61M 5/347 |
| | | | | 604/110 |
| 5,047,017 | A * | 9/1991 | Koska | A61M 5/5066 |
| | | | | 604/110 |
| 5,267,962 | A | 12/1993 | Jenson | |
| 6,368,306 | B1 * | 4/2002 | Koska | A61M 5/5066 |
| | | | | 604/218 |
| 6,972,006 | B2 * | 12/2005 | Ferguson | A61M 5/3129 |
| | | | | 604/186 |
| 8,016,787 | B2 * | 9/2011 | Gramage Pina | A61M 5/5013 |
| | | | | 604/110 |
| 2003/0097096 | A1 * | 5/2003 | Niedospial, Jr. | A61M 5/3129 |
| | | | | 604/218 |
| 2004/0186428 | A1 * | 9/2004 | Ray | A61M 5/50 |
| | | | | 604/110 |
| 2009/0159813 | A1 * | 6/2009 | Kemp | A61L 2/10 |
| | | | | 250/455.11 |
| 2010/0049124 | A1 * | 2/2010 | Gramage Pina | A61M 5/5013 |
| | | | | 604/110 |
| 2013/0310741 | A1 | 11/2013 | Gramage Pina | |

FOREIGN PATENT DOCUMENTS

| | | | |
|---|---|---|---|
| EP | 2103321 A1 * | 9/2009 | |
| ES | 2012198 | 3/1990 | |
| ES | 2014802 | 7/1990 | |
| ES | 1055675 U | 1/2004 | |
| WO | WO2008/084124 A1 * | 7/2008 | |
| WO | WO 2008/084124 A1 | 7/2008 | |

* cited by examiner

SINGLE-USE SYRINGE

CROSS-REFERENCE TO RELATED APPLICATIONS

This application is a National Phase Application of PCT International Application No. PCT/ES2010/000469, International Filing Date Nov. 18, 2010, which is hereby incorporated by reference.

FIELD OF THE INVENTION

The present invention relates to a self-disabling or self-locking single-use passive syringe, i.e., it is locked after the first use of the syringe, regardless of the user's wishes.

OBJECT OF THE INVENTION

The object to which the protected invention relates consists of a single-use syringe with a plunger locking and breaking system for preventing reuse.

A syringe which is locked after the first use and reuse of which is materially impossible is necessary in today's society not only because of the problems generated in drug addicts and in underdeveloped countries, where the same syringe is often used in thirty patients, but also because of the existence of so-called clinical errors in hospitals of developed countries, these being 0.3% annually.

The WHO, Red Cross, Red Crescent Movement, Anti-AIDS Foundation and UNICEF urged at the end of 2003 for today's society to provide a passive action self-locking or self-disabling syringe, i.e., the syringe must break or lock after first use with or without the user's intention. Multinational manufacturers of these products are working on manufacturing a syringe which provides all the advantages of a conventional syringe and eliminates all the drawbacks. This has resulted in an important number of locking or disabling syringes being registered as prior art.

From what can be seen in all of them, none has been able to combine all the advantages of conventional syringes incorporating the impossibility of reuse. In patent PCT/ES2007/070001 from the same applicant, the syringe overcomes the drawbacks of syringes existing in the prior art, and specifically prevents causing bruises in the patient, while at the same time conserving the self-locking features after the first use, eliminating the possibility of the user manipulating the locking system, and simplifying the construction of the locking system. However, it has manufacturing problems which have been solved in the present invention.

In this new syringe, in addition to all the foregoing advantages, the following must be included:

It can be manufactured in all the millimetric capacities existing in conventional use syringes.

It can indistinctly be manufactured in two or three bodies, thus covering the private and public market, the latter being very important, not contemplated in the prior art.

It can be manufactured in all cone models (the cone is the appendage extending from the body of the syringe where the needle is located or inserted), both concentric cone and eccentric cone.

With this new self-locking or self-disabling syringe model it can be clearly said that all the advantages of a conventional syringe are combined, all the drawbacks of the prior art are eliminated, all at the same manufacturing cost as that of conventional syringes and therefore covering all the global public and private syringe markets since no prior art covers both.

The single-use syringe of the invention includes a barrel or body of the syringe thickened in some of its parts; the locking means will thus be ring-shaped in the form of grooves in the thickened parts, instead of the entire barrel having a uniform thickness and placing thicknessings or protrusions or rings inside the barrel.

The single-use syringe of the invention incorporates a plunger in which each longitudinal fin (2) has a different height, such that the plunger cannot rotate about itself (spin movement) inside the barrel or body of the syringe, whereby preventing, with a rotation while the plunger is being extracted, fins (7) or locking "wings" from being bent and the plunger from being removed, preventing breaking.

The single-use syringe of the invention achieves improved leak-tightness because the plunger cannot rotate about itself, and better and greater ease and precision when pushing and pulling the plunger, since it cannot rotate about itself.

This new shape further allows it to be manufactured in two and three bodies (private and public health care) and in all millimetric capacities, being able to be adapted to all the configurations and services offered by current conventional syringes which do not lock or break after use, including syringes for drug addicts.

Finally, the manufacturing cost is comparable to that of conventional syringes manufactured today, which do not lock or break after use

BACKGROUND OF THE INVENTION

The closest background of this invention is patent PCT PCT/ES2007/070001 from the same applicant in which a single-use syringe which could be considered the blueprint of the current invention is claimed. In said patent, the anchoring rings protruded from the barrel or body of the syringe into same, which is difficult to manufacture. However, in a conventional syringe in which the barrel is cylindrical and the walls of uniform thickness, providing perforated anchoring rings in the wall would mean a weakening of the walls, which is undesirable. The present invention solves these and other problems.

DESCRIPTION OF THE INVENTION

The purpose of the invention consists of overcoming the drawbacks of the syringe which have been detected in pre-manufacture engineering studies, having been contrived and designed with this priority objective in mind.

Generating grooves such as those depicted with numbers (8) and (9) of FIGS. (3) and (7) of the present invention is much more advantageous for manufacturing a syringe element than the thicknessings such as those depicted by numbers (8) and (9) of FIG. 1 of the present invention representing the prior art. There will thus be a barrel or body of the syringe (10) having an external shape of a cylinder of revolution with a constant radius circular base. However, said barrel will have a variable internal shape, generating a chamber the shape of which will be specified below. This generated internal chamber has one or several ring-shaped grooves (preferably two) the purpose of which is that the "fins" (7) of the plunger remain fit in these rings, said plunger breaking at the weakened area (5) located immediately after the "fins" (7) in the event that the user struggles with the plunger attempting to reuse it. In the prior art the barrel had the general shape of a cylinder formed by a cylinder with an external radius and an internal radius coaxial with the external cylinder but with a smaller radius whereby in short, a cylinder of uniform thickness is obtained between both cylinders. One or several rings (of variable radius) projected into (towards the longitudinal axis) the cylinder were added inside said cylinder. In the configuration of this invention, the body of the syringe has a fixed and constant external radius and variable internal radius such that a cylinder of variable thickness is generated; it is the wall (11) of the cylinder that has perforated ring-shaped grooves coaxial with the external cylinder of the body, the internal radius of which will generally be variable and the external radius of which is fixed and slightly less than the external radius of the barrel or body of the syringe.

BRIEF DESCRIPTION OF THE DRAWINGS

To complement the description of the invention and facilitate the interpretation of its formal, structural and functional features, drawings are attached in which different aspects of the single-use syringe forming the object of the present invention are schematically depicted.

In said drawings.

DETAILED DESCRIPTION OF THE INVENTION

The preferred embodiments of the invention, provided solely in an illustrative manner and in no way limiting the scope of the invention, will be described below in detail.

Preferred Embodiment 1

Figure 1:
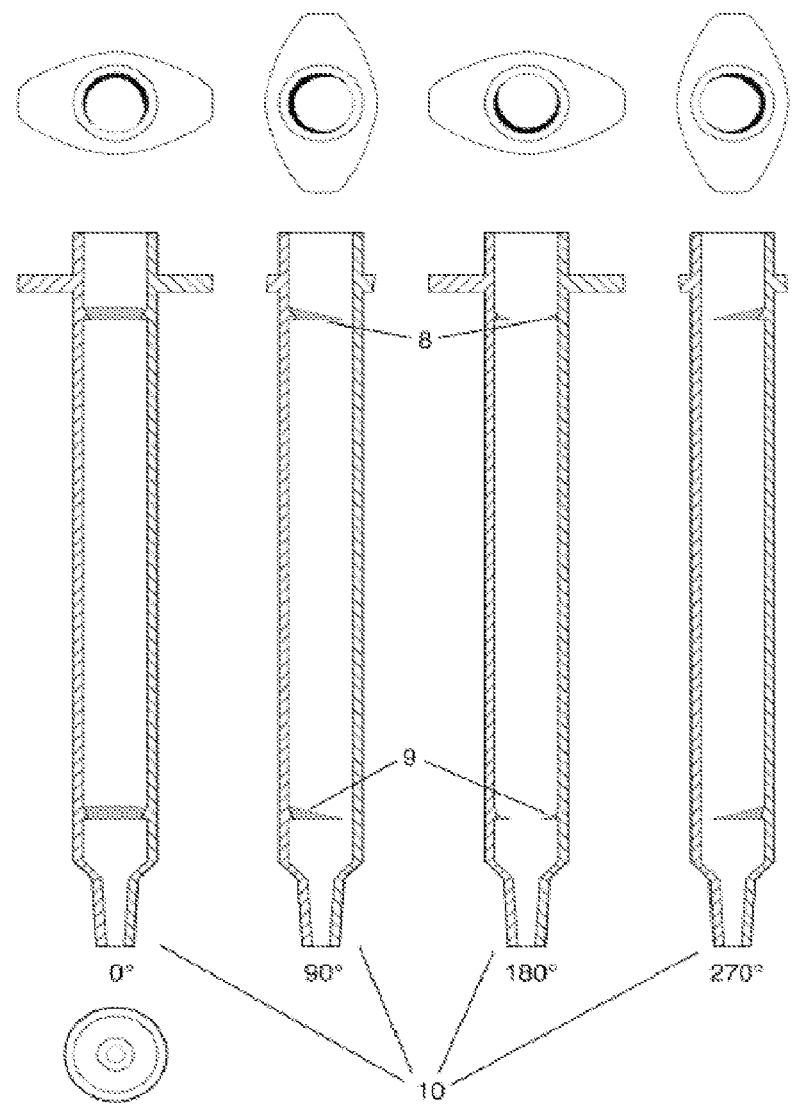
FIG. 1 of the present invention shows the prior art and corresponds to FIG. 3 of patent PCT/ES2007/070001; it shows the external body or barrel of the syringe.
Figure 2:
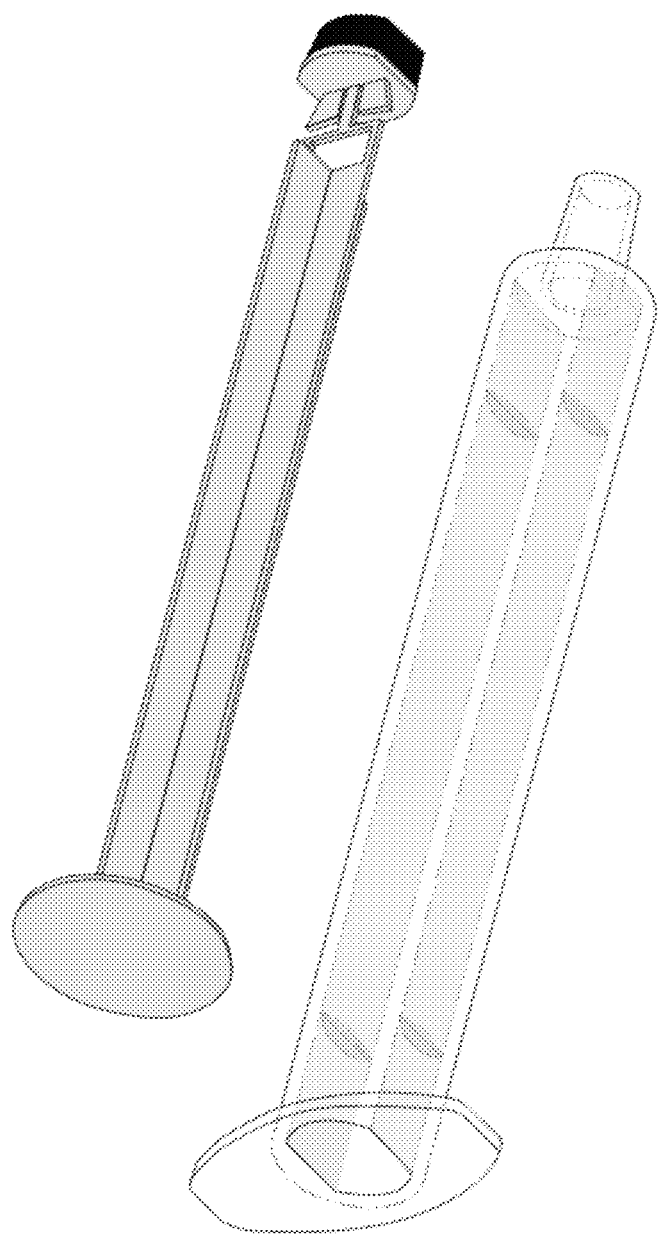
FIG. 2 of the present invention shows a three-dimensional perspective depiction of a first preferred embodiment of the invention, the external body or barrel of the syringe and the internal plunger being depicted in the same figure; each part is placed unassembled next to the other. In this case they take the form of a three-piece syringe: barrel, plunger and piston, where the piston is assembled in the plunger.
Figure 3:
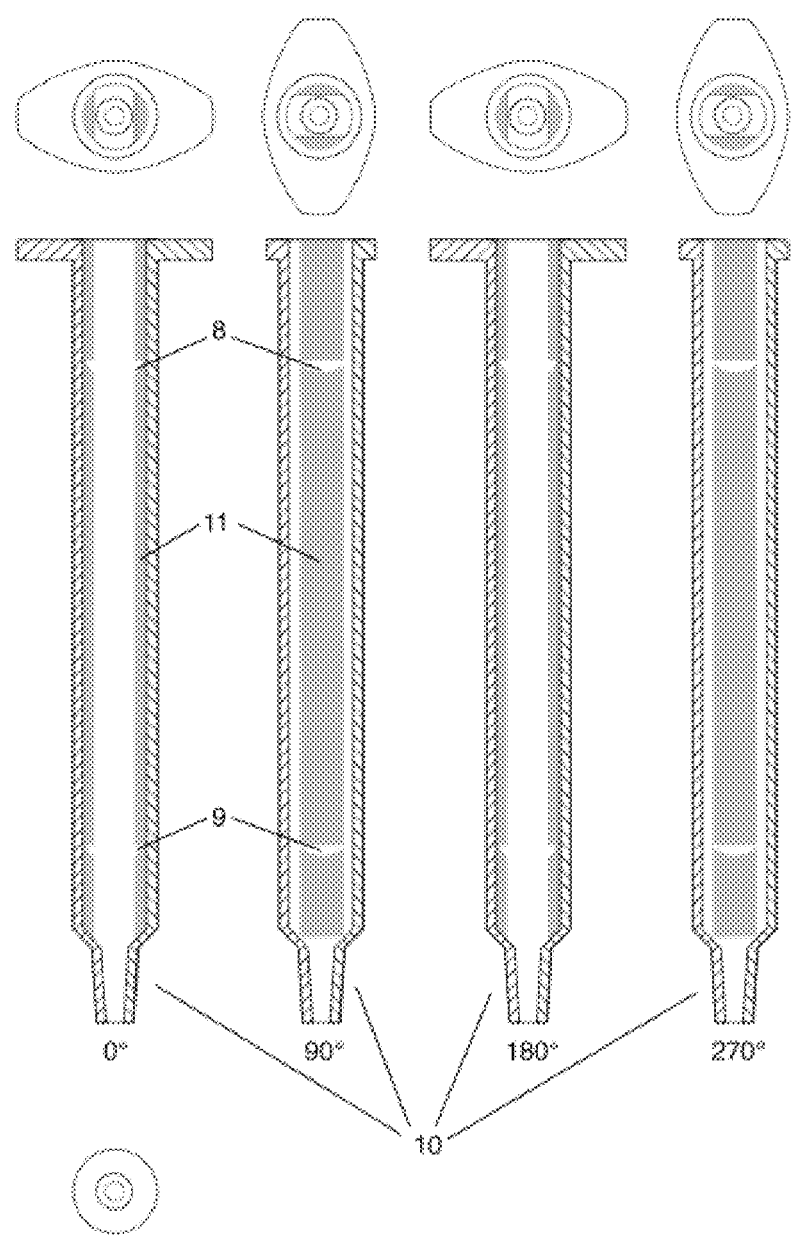
FIG. 3 of the present invention shows the external body or barrel of the syringe corresponding to the first preferred embodiment of the invention; said external body of the syringe is depicted in four side views displaced 90°, such that the invention is understood in depth at a single glance. Four plan views, one for each profile, are also included.

In a first preferred embodiment of the invention the syringe will include:

Barrel:

The barrel of the syringe is shown in detail in FIGS. 2 and 3. FIG. 2 consists of a three-dimensional view of the device of the first preferred embodiment; FIG. 3 incorporates the profile of the barrel used in the single-use syringe of the invention in views at intervals displaced 90°. Said barrel has a substantially cylindrical external shape with a circular base, i.e., with a fixed radius. A chamber having the general shape of a parallelepiped or rectangular prism with a square base is defined inside said barrel, the diagonal of which coincides with the internal theoretical diameter of the barrel to which two cylinder sectors of the same height have been attached and the radius of which (measured from the central axis of the prism) coincides with the internal theoretical radius of the barrel. Theoretical radius is considered to be that which a conventional syringe with the same capacity and the same external radius would have. A barrel is thus generated which, if divided into four sectors of 90 degrees, in two of them (opposite one another by the apex) there will be a general cylinder sector shape with a quarter ring-shaped base, formed between an external cylinder with a fixed and constant radius and an internal cylinder also with a fixed and constant radius, therefore a quarter cylinder of constant thickness similar to any of the conventional syringes used today is defined. The two other sectors will have a quarter cylinder shape with a circular sector base, such that the external part will correspond to a cylinder with the same radius than that of the two other aforementioned sectors, and the internal part will correspond to a "chord" or straight line drawn between the ends of the external cylinder quarter as seen in FIGS. 2, 3, 4 and 5. It can surprisingly be seen better in FIG. 4, corresponding to the plunger and not to the barrel, in the form of the piston, since it penetrates the barrel tightly, where the external shape of the piston necessarily has to be the internal shape of the barrel. The two circular sector-shaped grooves with a substantially triangular section and variable radius located in the part furthest from the needle (8) and part closest to the internal needle (9) of the barrel respectively can be seen in the internal part of the barrel corresponding to the inwardly thickened walls (11); the circular sectors have a substantially triangular section and a general circular crown shape with a variable internal radius, such that the external radius of each ring will always be the internal theoretical radius of the barrel (in the event that the inside was cylindrical), and the internal radius of each ring will be variable, such that, such that they preferably have at both ends an internal radius equal to the internal radius of the barrel (see view at 0°), while the internal radius in the centre of each circular sector is minimum (see views at 90° and 270°). The general shape of the two grooves is wedge or triangular shaped, generally a right-angled triangle shape, such that the plunger can be inserted into the barrel but cannot be easily extracted.

In an alternative embodiment of this preferred embodiment of the invention, there could be one or even three or more areas of walls thickened inwardly in the barrel instead of two.

The distance from the circular sector-shaped grooves to the end of the barrel closest to the needle can be varied such that the amount of liquid volume which can be injected and/or pumped repeatedly can be chosen before the plunger is locked. Therefore, while it is convenient for the ring furthest from the position of the needle to be close to the distal end of the barrel with respect to the needle for the purpose of maximising the useful volume, the ring closest to the position of the needle can be located in a position closer to or further from the proximal end of the barrel with respect to the needle, separated from said end by a greater or smaller distance, generating a chamber with a larger or smaller size, but in any case preferably inside the first third of the length of the barrel with respect to the needle. Therefore, if the lower ring is located in a position further from the barrel with respect to the end of the needle, the plunger will be locked when a smaller liquid volume is injected into the user. If, on the other hand, the groove (9) is located in a position closer to the proximal end of the barrel with respect to the needle, there is a larger useful injectable liquid volume before the plunger is locked, which could be used by a drug addict user to reuse the syringe many times without reaching the locking position of the plunger. The groove (9) closest to the end where the needle is located will preferably be placed in a position close to the end of the first third of the length of the barrel with respect to the end close to the needle.

The angle formed by the grooves with respect to the axis of the syringe is also susceptible to variation, such that the grooves do not necessarily have to be perpendicular to the axis of the cylinder, but they could be placed diagonally with an angle with respect to the axis other than 90°.

Figure 4:
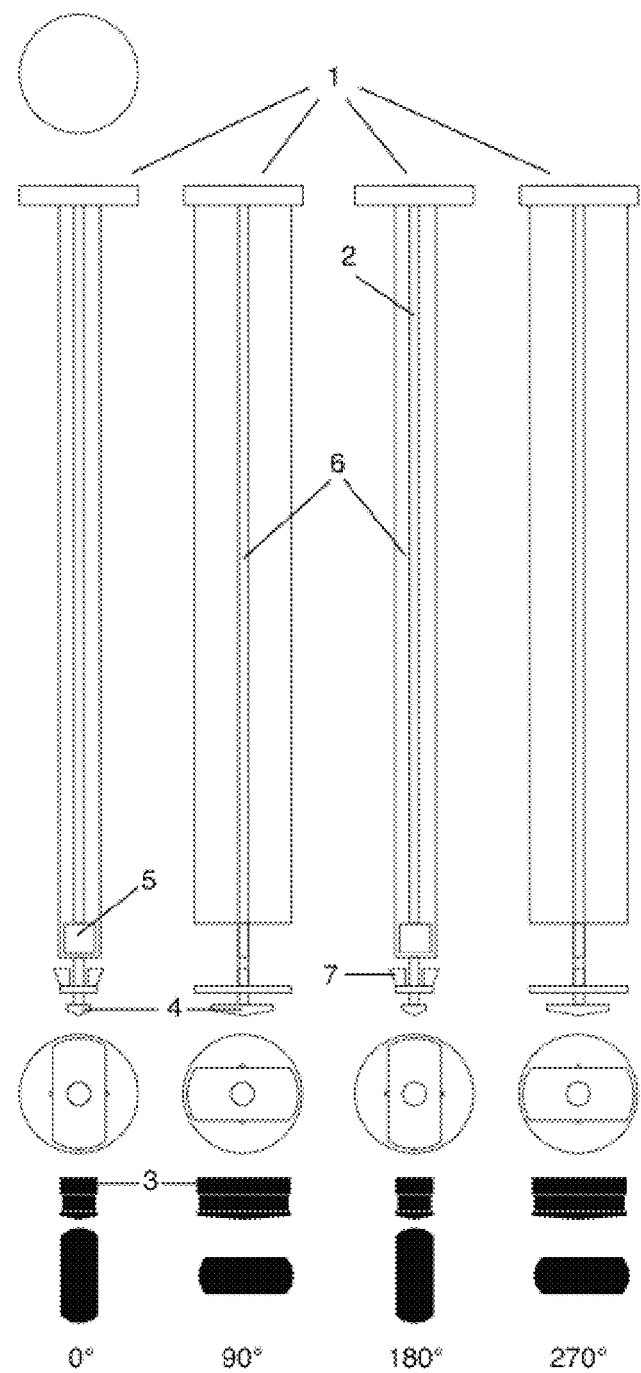
FIG. 4 of the present invention shows the plunger of the syringe or internal part of the syringe corresponding to the first preferred embodiment of the invention, which moves through the inside of the barrel, in this case for a three-piece syringe, i.e., a syringe incorporating a rubber piston or the like at the end of the plunger closest to the needle. Four views corresponding to the same plunger in four positions displaced 90° can be seen.
Figure 5:
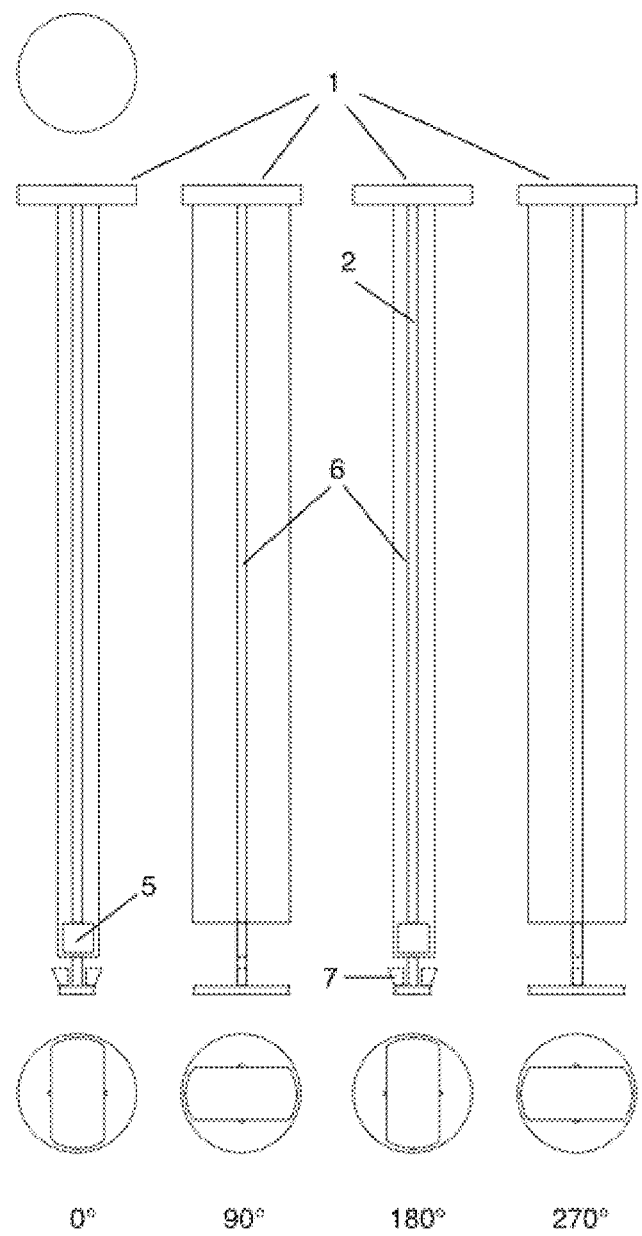
FIG. 5 of the present invention shows the plunger or internal part of the syringe corresponding to the first preferred embodiment of the invention, which moves through the inside of the barrel, in this case for a two-piece syringe, i.e., barrel and plunger "without a piston", instead of the case of FIG. 4 which was for syringes with three bodies.

Plunger:

The plunger of the first preferred embodiment of the invention is depicted in detail in FIGS. 4 and 5. They show that the plunger comprises an elongated body defining a longitudinal axis, said elongated body comprising a plurality of longitudinal fins (2) running substantially along the entire length of the plunger; each of the longitudinal fins (2) of the plunger has a constant height along its entire length but different from the height of the other fins, suitable so that the plunger (1) can be inserted tightly through the space defined by the inside of the barrel. The length of at least one of the longitudinal fins (2) is also different from the length of at least one of the other longitudinal fins (2) so that the plunger includes a weakened area in the form of a hole at the end of the plunger close to the needle. The number of longitudinal fins (2) is preferably four, since this is the number of longitudinal fins present in conventional syringes. However, the invention is not limited by the number of longitudinal fins, and any number of longitudinal fins is acceptable provided that their number and height are variable such that the plunger can be inserted tightly through the space defined by the walls (11) of the barrel, which in turn also have a variable internal radius. On the other hand not necessarily all the longitudinal fins (2) have to have a height different from the rest, several of them being able to be equal in height, or some being able to be of the same height and the rest of different heights. The plunger further comprises a weakened area (5) preferably located at the end close to the needle of the body of the plunger, and can have any shape, preferably being a circular- or polygonal-shaped, generally triangular or square-shaped, hole.

FIG. 4 shows the plunger of the first preferred embodiment of the syringe or internal part which moves through the inside of the barrel, in this case for a three-piece syringe, i.e., a syringe incorporating a rubber "piston" or the like at the end of the plunger. Four profile and plan views can be seen corresponding to the same plunger in four positions displaced 90°, the profile and plan of the piston also being depicted in the same four positions.

FIG. 4 shows how the plunger (1) comprises a plurality of fins (2), preferably four, running longitudinally along the plunger to its end part, where the piston (3), typically a rubber part, is located, separated from the plunger by a connector (4). There is a weakened area in the form of a hole at the end of the plunger close to the needle which will generally have a variable shape, preferably polygonal (5) for the purpose of favouring its easy breaking through the angles of the polygon. In the embodiment shown in the figure, said hole is square-shaped. Each of the fins has a different height, which height is suitable in each case so that the plunger can be inserted tightly through the space defined by the barrel, having a variable internal radius. In this specific case there are fins of the same height, and the other two are also of the same height with respect to one another but different from the height of the first two. The length of the fins of the plunger will also preferably be different, being longer in those cases in which the projection of the fins towards the needle gives rise to the part of the plunger provided with a preferably polygonal internal hole defined previously (see views at 0° and 180° of FIG. 4).

FIG. 5 shows the plunger of the first preferred embodiment of the syringe or internal part which moves through the inside of the barrel, but for the case of a syringe with two bodies (barrel and plunger, "without a piston") instead of the case of FIG. 4, which was for syringes with three bodies "with a piston". FIG. 5 depicts the plunger of the syringe in four profile views displaced 90°, such that the invention is understood in depth at a single glance. Four plan views, one for each profile, are also included. This figure shows how the plunger (1) comprises a plurality of fins (2), preferably four, running longitudinally along the plunger to its end part. There is a weakened area in the form of a hole at the end of the plunger close to the needle which will generally have a variable shape, preferably polygonal (5) for the purpose of favouring its easy breaking through the angles of the polygon. In the embodiment shown in FIG. 5, said hole is square-shaped. Some of the fins have or can have a height different from the rest, which height is suitable in each case so that the plunger can be inserted tightly through the space defined by the barrel, having a variable internal radius. In this specific case there are fins of the same height, and the other two are also of the same height with respect to one another but different from the height of the first two. The length of the fins of the plunger will also preferably be different, being longer in those cases in which the projection of the fins towards the needle gives rise to the part of the plunger provided with a preferably polygonal internal hole defined previously (see views at 0° and 180° of FIG. 5).

Preferred Embodiment 2

Figure 6:
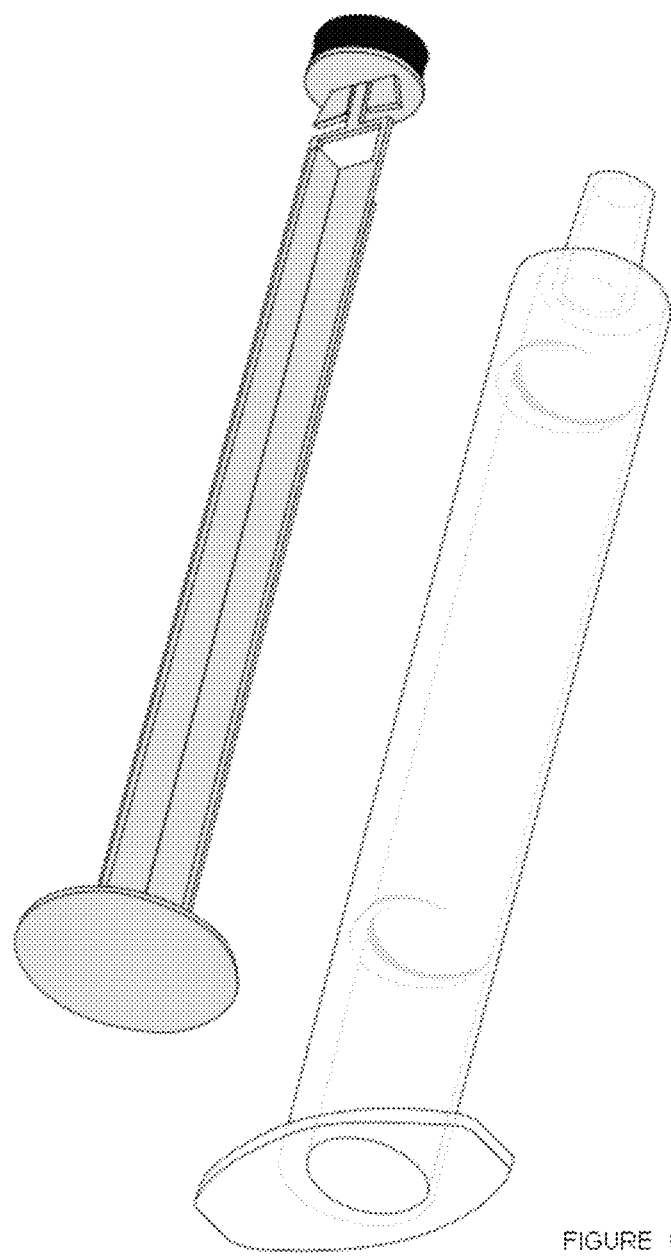
FIG. 6 of the present invention shows a three-dimensional perspective depiction of a second preferred embodiment of the invention, the external body or barrel of the syringe and the internal plunger being depicted in the same figure; each part is placed unassembled next to the other. In this case they take the form of a three-piece syringe: barrel, plunger and piston, where the piston is assembled in the plunger.

A second preferred embodiment of the invention can be seen in FIGS. 6, 7, 8 and 9. FIG. 6 shows a three-dimensional depiction of the syringe, with the barrel and the plunger separated, unassembled. The external body or barrel of the syringe and the internal plunger are depicted in the same figure; each part is placed unassembled next to the other. In this case they take the form of a three-piece syringe: barrel, plunger and piston, where the piston is assembled in the plunger.

Figure 7:
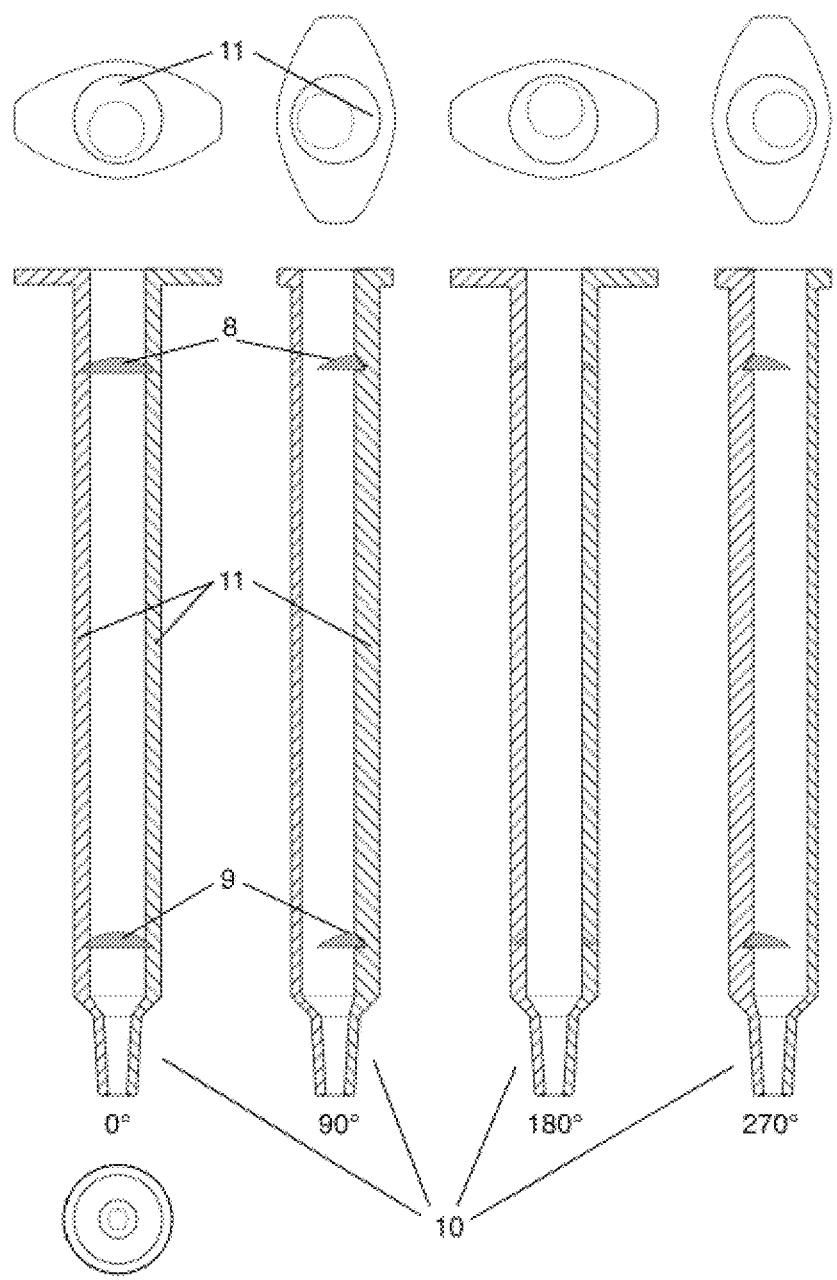
FIG. 7 of the present invention shows the external body or barrel of the syringe corresponding to the second preferred embodiment of the invention; said external body of the syringe is depicted in four side views displaced 90°, such that the invention is understood in depth at a single glance. Four plan views, one for each profile, are also included.

The syringe according to the second preferred embodiment will include:
Barrel:

The barrel of the syringe is shown in detail in FIG. 7. FIG. 7 shows the barrel used in the single-use syringe of the invention in views at 90° intervals. Said barrel has a substantially cylindrical external shape with a circular base, i.e., with a fixed radius. The internal surface of said cylinder will be formed by a second cylinder with a radius smaller than that of the external cylinder, but not coaxial, but its axis is parallel to that of the external cylinder. If the obtained shape is analysed there will be a point in which the thickness of the wall (11) is minimum, similar to the thickness of current syringes, and said thickness will increase in both directions until it will be of maximum thickness at the diametrically opposite end. The two circular sector-shaped grooves with a substantially triangular section and variable radius located in the part further from the needle (8) and close to the internal needle (9) of the barrel respectively can be seen in the internal part of the barrel corresponding to the thickened wall (11); the grooves have a substantially triangular section and a general circular crown shape with a variable internal radius, always measured from the axis of the external cylinder of the barrel and such that the external radius of each ring will always be the internal theoretical radius of the barrel (in the event that the inside was cylindrical coaxial and coincides with the radius at the point where the wall thickness is minimum), and the internal radius of each ring will be variable coinciding with the wall (11) of the internal cylinder. In some embodiments of the invention, at least one of the grooves has a generally triangular section in the form of a right-angled triangle, one of the legs being located adjacent to the internal wall of the barrel, the second leg being located perpendicular to said internal wall, and the hypotenuse between both legs forming an inclined plane in the forward direction of the plunger. In some embodiments of the invention, at least one of the grooves has a generally triangular section in the form of a right-angled triangle, wherein the hypotenuse is curved.

The distance from the grooves to the end of the barrel closest to the needle can be varied such that the amount of liquid volume which can be injected and/or pumped repeatedly can be chosen before the plunger is locked. Therefore, while it is convenient for the ring furthest from the position of the needle to be close to the distal end of the barrel with respect to the needle for the purpose of maximising the useful volume, the ring closest to the position of the needle can be located in a position closer to or further from the proximal end of the barrel with respect to the needle, separated from said end by a greater or smaller distance, generating a chamber with a larger or smaller size, but in any case preferably inside the first third of the length of the barrel with respect to the needle. Therefore, if the lower ring is located in a position further from the barrel with respect to the end of the needle, the plunger will be locked when a smaller liquid volume is injected into the user. If, on the other hand, the groove (9) is located in a position closer to the proximal end of the barrel with respect to the needle, there is a larger useful injectable liquid volume before the plunger is locked, which could be used by a drug addict user to reuse the syringe many times without reaching the locking position of the plunger. The groove (9) closest to the end where the needle is located will preferably be placed in a position close to the end of the first third of the length of the barrel with respect to the end close to the needle.

The angle formed by the grooves with respect to the axis of the syringe is also susceptible to variation, such that the grooves do not necessarily have to be perpendicular to the axis of the cylinder, but they could be placed diagonally with an angle with respect to the axis other than 90°.

Figure 8:
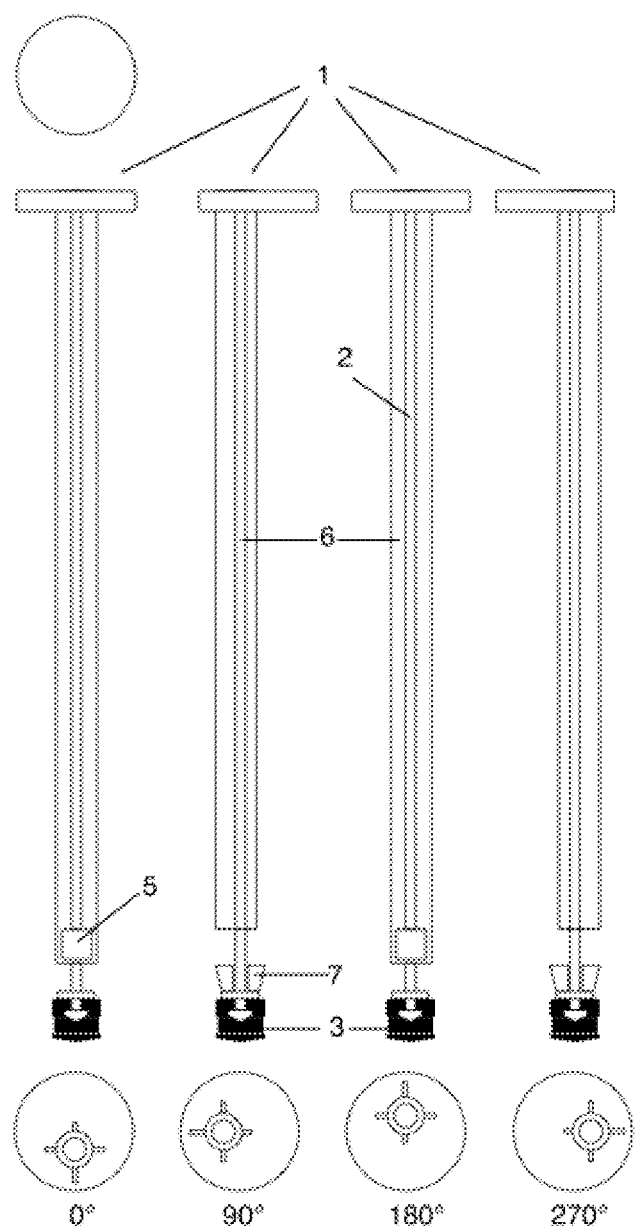
FIG. 8 of the present invention shows the plunger of the second preferred embodiment of the syringe or internal part which moves through the inside of the barrel, in this case for a three-piece syringe, i.e., a syringe incorporating a rubber piston or the like at the end of the plunger closest to the needle. Four views corresponding to the same plunger in four positions displaced 90° can be seen.
Figure 9:
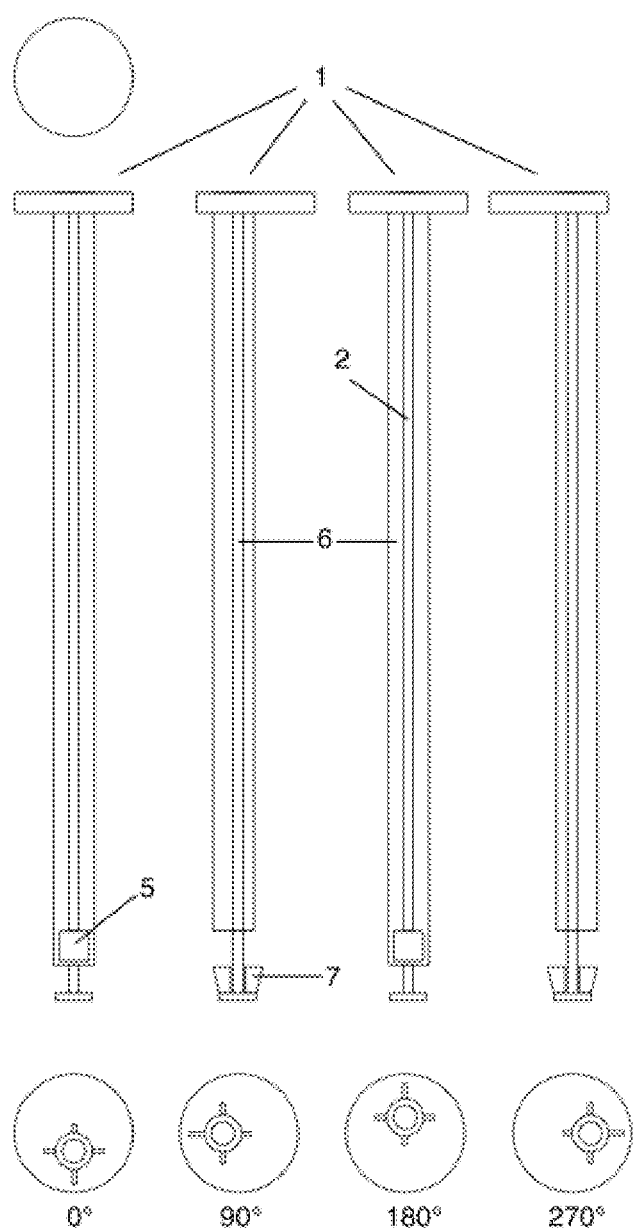
FIG. 9 of the present invention shows the plunger of the second preferred embodiment of the syringe or part which moves through the inside of the barrel, but for the case of a syringe with two bodies, i.e., barrel and plunger, "without a piston", instead of the case of FIG. 8 which is for syringes with three bodies.

Plunger:

The plunger is depicted in detail in FIGS. 8 and 9. They show that the plunger comprises an elongated body defining a longitudinal axis corresponding to the axis of the external cylinder of the barrel or body of the syringe, said elongated body comprising a plurality of longitudinal fins (2) running substantially along the entire length of the plunger, and each of the longitudinal fins (2) of the plunger has a constant height along the entire length but different from the height of the other fins, suitable so that the plunger (1) can be inserted tightly through the space defined by the inside of the barrel. The length of at least one of the fins is also different from the length of at least one of the other fins so that the plunger includes a weakened area in the form of a hole at the end of the plunger close to the needle. The number of fins is preferably four, since this is the number of fins present in conventional syringes. However, the invention is not limited by the number of fins, and any number of fins is acceptable provided that their number and height are variable such that the plunger can be inserted tightly through the space defined by the walls of the barrel, which in turn also have a variable internal radius. The plunger further comprises a weakened area (5) preferably located at the end close to the needle of the body of the plunger, and can have any shape, preferably being polygonal-shaped, generally triangular or square-shaped.

In this particular case there would be a fin (2) of maximum height, two equal fins (2) of medium height and a fin (2) of minimum height.

In the configuration of the three-piece syringe of FIG. 8, there will be a connector attaching the plunger with the piston (3), which is usually a rubber part, the external surface of which is in leak-tight connection with the internal surface of the barrel and to that end has its shape.

FIG. 9 shows an alternative embodiment with respect to the plunger of FIG. 8, which is a two-piece syringe with a configuration similar to the preceding one but without the piston.

Having described the nature and the functional scope of the invention as well as a preferred form of putting it into practice, it is hereby stated that the materials, shapes, dimensions and generally all those accessory or secondary features which do not alter, change or modify the essential nature of the invention detailed in the following claims can be varied.

The invention claimed is:

1. Single-use syringe comprising a barrel having
   an internal surface defining a chamber for retaining a fluid,
   a plunger formed by an elongated body including a plurality of longitudinal fins and optionally a piston connected to an end of the plunger close to a needle, an external surface of the piston or of the end of the plunger in the case of not including a piston being in leak-tight connection with an internal surface of the barrel, wherein the barrel has a general external shape of a cylinder of revolution with a constant radius circular base and a variable internal shape, forming a wall of the barrel with variable thickness, generating a chamber inside which the plunger incorporating the plurality of longitudinal fins slides;

wherein each of the longitudinal fins of the plunger has a constant height along its entire length but different from that of at least one of the other longitudinal fins, which constant height is suitable in each longitudinal fin so that the plunger can be inserted tightly without the capability of rotating about itself through a space defined by a variable internal radius of the barrel;

wherein a length of at least one of the longitudinal fins is also different from a length of at least one of the other longitudinal fins so that the plunger includes a weakened area in the form of a hole at the end of the plunger close to the needle; and wherein the barrel further comprises at least two grooves in the internal surface of the barrel, at least one being located in a distal part and at least one in a proximal part of the barrel with respect to the needle.

2. Single-use syringe according to claim 1, wherein the variable internal shape of the barrel is a cylinder with a circular base.

3. Single-use syringe according to claim 1, wherein the variable internal shape of the barrel is a cylinder not coaxial with the general external shape of the cylinder.

4. Single-use syringe according to claim 1, wherein the variable internal shape of the barrel is a cylinder of revolution with a circular base with a smaller diameter than the external cylinder and not coaxial with it.

5. Single-use syringe according to claim 1, wherein the variable internal shape of the barrel is a parallelepiped with one or more cylinder sectors placed against one another in one or several of their faces.

6. Single-use syringe according to claim 1, wherein the variable internal shape of the barrel is a prism.

7. Single-use syringe according to claim 1, wherein the general external shape of the barrel is a cylinder with a circular base.

8. Single-use syringe according to claim 1, wherein the variable internal shape of the barrel is a prism.

9. Single-use syringe according to claim 1, wherein the plunger is attached to a piston at the end closest to the needle by means of a connector forming part of the plunger itself.

10. Single-use syringe according to claim 1, wherein at least one of the grooves is not a closed ring and does not completely surround the internal surface of the barrel.

11. Single-use syringe according to claim 1, wherein at least one of the grooves is perpendicular to a longitudinal axis of the barrel.

12. Single-use syringe according to claim 1, wherein at least one of the grooves has a substantially triangular section and a general circular crown shape with a variable internal radius.

13. Single-use syringe according to claim 1, wherein at least one of the grooves has a generally triangular section in the form of a right-angled triangle, one of the legs being located adjacent to the internal surface of the barrel, the second leg being located perpendicular to said internal wall, and the hypotenuse between both legs forming an inclined plane in a forward direction of the plunger.

14. Single-use syringe according to claim 1, wherein at least one of the grooves has a generally triangular section in the form of a right-angled triangle, wherein the hypotenuse is curved.

15. Single-use syringe according to claim 1, wherein the variable thickness of the wall of the barrel is variable in a cross section view perpendicular to a longitudinal direction.

* * * * *